United States Patent
Kim et al.

(10) Patent No.: US 10,130,254 B2
(45) Date of Patent: Nov. 20, 2018

(54) CELL-LEVEL RETINAL DISEASE DETECTION APPARATUS

(71) Applicant: Korea Institute of Science and Technology, Seoul (KR)

(72) Inventors: Jae Hun Kim, Seoul (KR); Seok Hwan Kim, Seoul (KR); Ju Yeong Oh, Seoul (KR); Byeong Ho Park, Seoul (KR); Hyo Suk Kim, Seoul (KR); Min Ah Seo, Seoul (KR); Chul Ki Kim, Seoul (KR); Taik Jin Lee, Seoul (KR); Deok Ha Woo, Seoul (KR); Seok Lee, Seoul (KR); Young Min Jhon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/472,439

(22) Filed: Mar. 29, 2017

(65) Prior Publication Data

US 2018/0078132 A1    Mar. 22, 2018

(30) Foreign Application Priority Data

Sep. 22, 2016 (KR) .......................... 10-2016-0121456

(51) Int. Cl.
*A61B 3/12* (2006.01)
*A61B 3/10* (2006.01)
(Continued)

(52) U.S. Cl.
CPC .............. *A61B 3/12* (2013.01); *A61B 3/1015* (2013.01); *G02B 26/06* (2013.01);
(Continued)

(58) Field of Classification Search
CPC ....... A61B 3/1225; A61B 3/14; A61B 3/1005; A61B 3/12; A61B 3/1025
(Continued)

(56) References Cited

U.S. PATENT DOCUMENTS 6,810,140 B2 * 10/2004 Yang ...................... A61B 3/102
351/240
9,028,067 B1 * 5/2015 Fleischman ............ A61B 3/113
351/209
(Continued)

FOREIGN PATENT DOCUMENTS

JP    2007-296209 A    11/2007

OTHER PUBLICATIONS

Korean Office Action dated Dec. 27, 2017 in corresponding Korean Patent Application No. 10-20165-0121456 (1 pages in English and 5 pages in Korean).

*Primary Examiner* — Mohammed Hasan
(74) *Attorney, Agent, or Firm* — NSIP Law

(57) ABSTRACT

Provided is a cell-level retinal disease detection apparatus including a light imaging means configured to emit light to an eyeball and a light processing means which receives light reflected by the eyeball and processes and compensates light for an astigmatism aberration thereof which occurs at the eyeball to compensate. Here, the light processing means includes a wavefront sensor which senses the astigmatism aberration of the reflected light which occurs due to the eyeball and a light compensation mirror which compensates the light based on the sensed astigmatism aberration, and compensates for a difference in the astigmatism aberration to detect a disease of a retina of the eyeball.

5 Claims, 4 Drawing Sheets

(51) Int. Cl.
*G02B 27/00* (2006.01)
*G02B 27/28* (2006.01)
*G02B 26/06* (2006.01)
*G02B 5/30* (2006.01)

(52) U.S. Cl.
CPC ....... *G02B 27/0068* (2013.01); *G02B 27/283* (2013.01); *G02B 5/3025* (2013.01)

(58) Field of Classification Search
USPC .................................................. 351/200–246
See application file for complete search history.

(56) References Cited

U.S. PATENT DOCUMENTS

| | | | |
|---|---|---|---|
| 2012/0044456 A1* | 2/2012 | Hayashi ................. | A61B 3/102 351/206 |
| 2015/0036103 A1* | 2/2015 | Kitamura ............... | A61B 3/102 351/206 |
| 2016/0265899 A1 | 9/2016 | Minemura et al. | |

* cited by examiner

CELL-LEVEL RETINAL DISEASE DETECTION APPARATUS

CROSS-REFERENCE TO RELATED APPLICATION

This application claims priority to and the benefit of Korean Patent Application No. 2016-0121456, filed on Sep. 22, 2016, the disclosure of which is incorporated herein by reference in its entirety.

BACKGROUND

1. Field of the Invention

The present invention relates to a cell-level retinal disease detection apparatus to which an active optical technology is applied to overcome an astigmatism aberration which occurs while light passes through a crystalline lens and a cornea.

2. Discussion of Related Art

It is difficult to detect diseases related to retinas such as glaucoma, macular degeneration, etc. due to the characteristic of cells and tissue thereof in which the diseases occur. Since layers of retina and cells which form the same are transparent, it is not easy for direct measurement using a general inspection method. Accordingly, several technologies are provided to detect related diseases. One of those enabling retinal cell imaging is a method of utilizing a differential interference contrast (DIC) microscopy.

The DIC is an apparatus which divides light into two paths with a micro difference therebetween and detects an optical distance between the two light paths with interference. Accordingly, since it is possible to image using interference when a difference of an optical distance occurs, imaging of a transparent material to be measured is possible. Here, since a retina includes cell layers which are transparent and have different functions as described above, even though a DIC is appropriate for imaging the retina, following means is necessary to overcome it.

The shape of optical beam after passing through a crystalline lens and a cornea is not completely regular since an astigmatism aberration occurs.

Also, since a retina is present at the back of an eyeball and has a spherical surface, a part of the surface comes into focus and another part thereof comes out of focus during imaging, thereby providing a narrow observation view (only partly focused).

Due to this, it is difficult to precisely detect a retinal disease using a conventional retina detection apparatus.

SUMMARY OF THE INVENTION

The present invention is directed to a cell-level retinal disease detection apparatus which overcomes an astigmatism aberration which occurs with light passing through a crystalline lens and a cornea and directly images transparent retinal cells.

The present invention is also directed to a cell-level retinal disease detection apparatus which overcomes having a narrow observation view caused by a distortion according to a shape of a retina.

According to an aspect of the present invention, there is provided a cell-level retinal disease detection apparatus including a light imaging means configured to emit light toward an eyeball and a light processing means which receives light reflected by the eyeball and processes and compensates light for an astigmatism aberration thereof which occurs at the eyeball, in which the light processing means includes a wavefront sensor which senses the astigmatism aberration of the reflected light which occurs due to the eyeball and a light compensation mirror which compensates the light based on the sensed astigmatism aberration for a difference in the astigmatism aberration to detect a disease of a retina of the eyeball.

The light imaging means may include a first polarizing plate which polarizes light emitted from a light source in one direction, a Wollaston prism which separates the polarized light, and an objective lens which transmits and converges the light separated by the Wollaston prism.

The Wollaston prism may be disposed close to the objective lens, and the light polarized by the first polarizing plate may be refracted by a predetermined angle by a beam splitter and may enter the Wollaston prism.

The light reflected by the eyeball may be detected by a second polarizing plate after passing through the Wollaston prism, and the detected light may enter the light processing means.

The Wollaston prism may be a first Wollaston prism disposed to be close to the first polarizing plate, and light passing through the first Wollaston prism may be refracted by a predetermined angle by a beam splitter and may enter the objective lens.

A separate second Wollaston prism for obtaining interference of a light signal by transmitting light compensated by the light processing means may be disposed close to the light processing means.

A second polarizing plate may be disposed close to the separate second Wollaston prism, and the second polarizing plate may detect light passing through the separate second Wollaston prism.

At least a part of the light compensated by the light compensation mirror may be refracted by a predetermined angle by a beam splitter.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
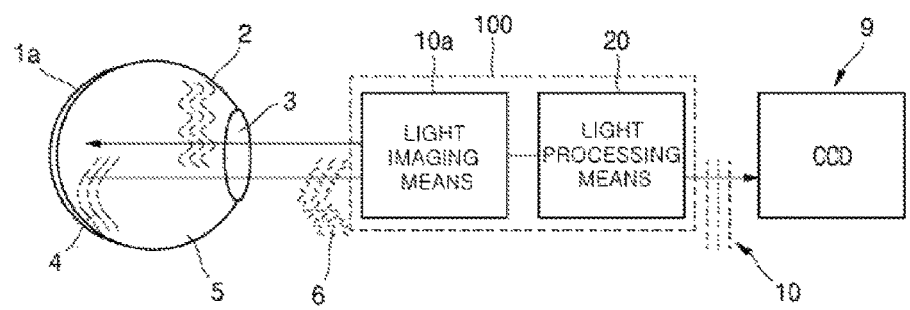
FIG. 1 is an overall concept view illustrating an example of using a cell-level retinal disease detection apparatus according to one embodiment of the present invention.

Hereinafter, embodiments of the specification will be described in detail with reference to the attached drawings. Like reference numerals refer to like elements, and a repeated description will be omitted. Since a non suffix "portion" for a component used below is given or mixed with something considering only the ease of drafting the specification, it does not have a differentiated meaning or function. In the description of the embodiments of the present invention, particular detailed explanations of well-known functions or components of the related art will be omitted when it is deemed that they may unnecessarily obscure the essence of the present invention. Also, the attached drawings are provided only for easy understanding of the embodiments disclosed in the specification, and it should be appreciated that the technical concept disclosed in the specification is not limited to the attached drawings and includes all modification, equivalents, and substitutes included within the concept and the technical scope of the present invention.

The terms first, second, etc. may be used for describing various components, but the components will not be limited by the terms. The terms are used only for distinguishing one element from another.

When it is stated that one component is "connected" to another component, it should be understood that it may be directly connected to the other component, but another component may exist therebetween.

Singular expressions, unless contextually otherwise defined, include plural expressions.

Also, throughout the specification, it should be understood that the terms "comprise", "have", etc. are used herein to specify the presence of stated features, numbers, steps, operations, elements, components or combinations thereof but do not preclude the presence or addition of one or more other features, numbers, steps, operations, elements, components, or combinations thereof.

Figure 2:
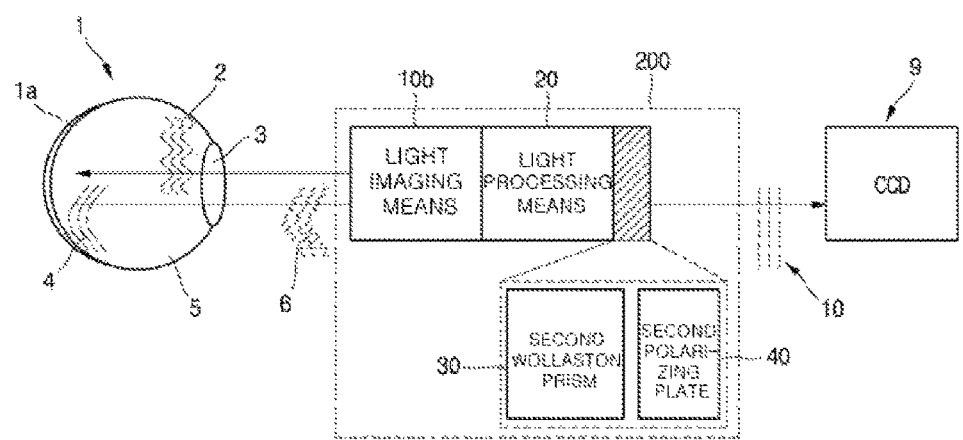
FIG. 2 is an overall concept view illustrating an example of using a cell-level retinal disease detection apparatus according to another embodiment of the present invention.
Figure 3:
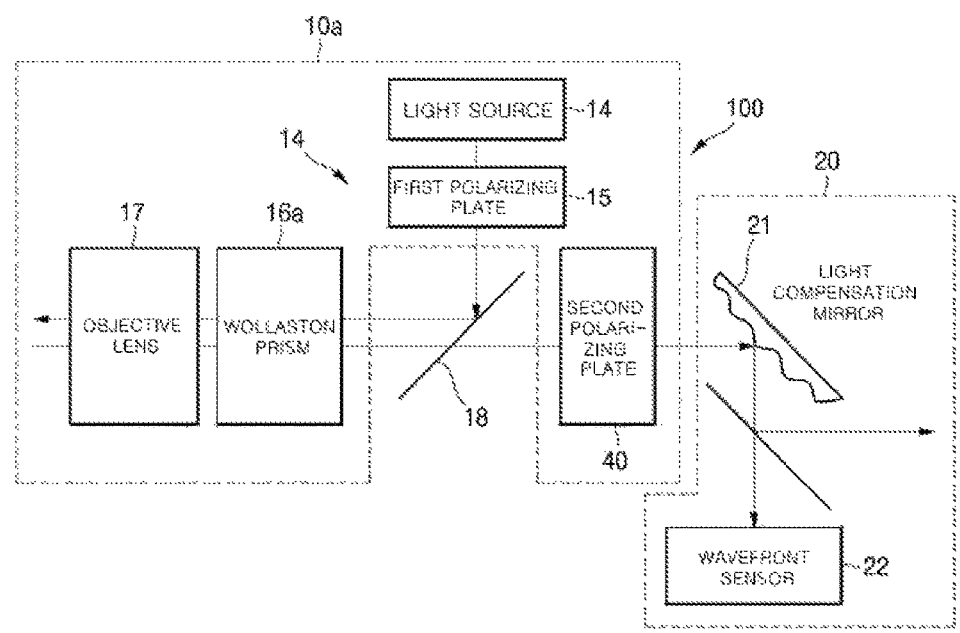
FIG. 3 is an enlarged concept view of the cell-level retinal disease detection apparatus of FIG. 1.
Figure 4:
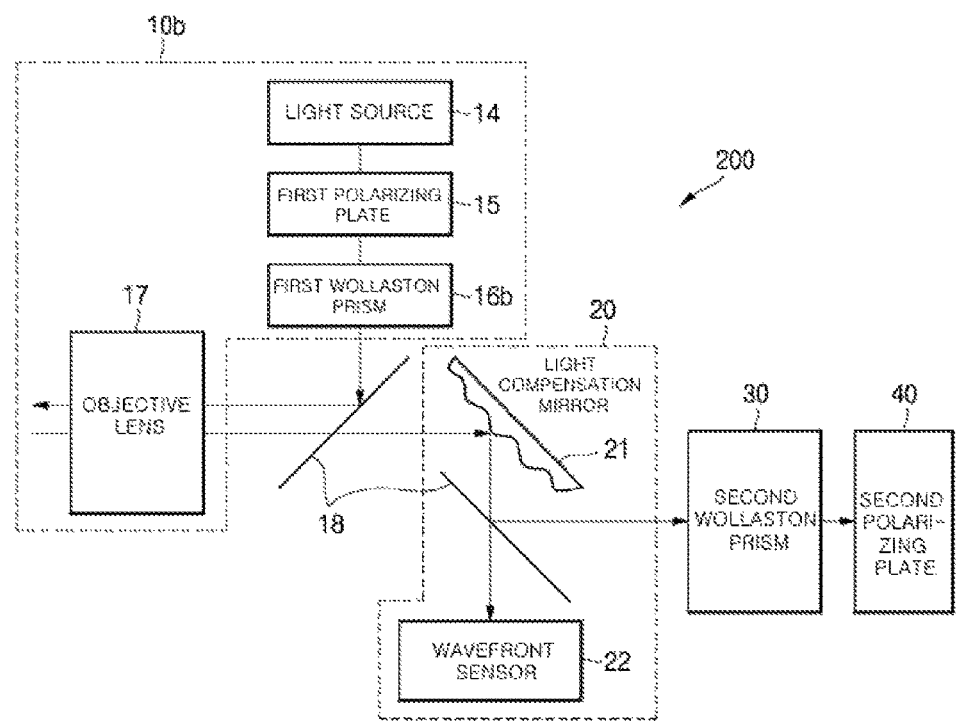
FIG. 4 is an enlarged concept view of the cell-level retinal disease detection apparatus of FIG. 2.

FIG. 1 is an overall concept view illustrating an example of using a cell-level retinal disease detection apparatus 100 according to one embodiment of the present invention. FIG. 2 is an overall concept view illustrating an overall example of using a cell-level retinal disease detection apparatus 200 according to another embodiment of the present invention. Also, FIG. 3 is an enlarged concept view of the cell-level retinal disease detection apparatus 100 of FIG. 1. FIG. 4 is an enlarged concept view of the cell-level retinal disease detection apparatus 200 of FIG. 2.

Hereinafter, referring to FIGS. 1 to 4, the cell-level retinal disease detection apparatuses 100 and 200 will be described.

The cell-level retinal disease detection apparatuses 100 and 200 include a light imaging means 10 and a light processing means 20.

The light imaging means 10 is formed to emit light to an eyeball 1. Light emitted toward the eyeball 1 is allowed to pass through a crystalline lens 3 and a vitreous body 5 and to be reflected by a retina 1a.

The light imaging means 10 may include a light source 14, a first polarizing plate 15, a Wollaston prism 16a, and an objective lens 17. Also, the light imaging means 10 may include a second polarizing plate 40 which is shown in FIG. 3. In the embodiment of FIG. 4 described below, the light imaging means 10 does not include the second polarizing plate 40.

The light source 14 generates light for observing the retina 1a, and for example, may include a fluorescent lamp, a mercury lamp, a sodium lamp, etc.

The first polarizing plate 15 separates only light polarized in one direction from light generated by the light source 14 to form a polarizing signal. For example, the first polarizing plate 15 may separate only light polarized at an arbitrary angle a from the light generated by the light source 14 to generate a light signal. The arbitrary angle a may be 45°.

The Wollaston prism 16a separates light polarized by the first polarizing plate 15.

The Wollaston prism 16a separates light incident on one path into lights on two paths. For example, the light with two paths has the same propagating direction, but polarization angles thereof meet each other at 90°. Accordingly, a first light may have a+45° and a second light may have a−45° compared with an angle at which the first light passes through the first polarizing plate 15.

Meanwhile, when the light separated into the light with two paths is incident, the Wollaston prism 16a may be integrated as a single light. For example, the first light and the second light return from a+45° and a−45° to a°.

The Wollaston prism 16a transmits and separates the light polarized by the first polarizing plate 15 into lights on two paths and integrates the lights on two paths which passes through the objective lens 17, is emitted to the eyeball 1, and then reflected by the eyeball 1 and returns therefrom into one. The light emitted to the eyeball 1 and the light reflected by the eyeball 1 may be separated or integrated.

The Wollaston prism 16a, as shown in FIG. 3, may be formed as one to separate and converge light at the same time, or as shown in FIG. 4, may be formed as two Wollaston prisms 16b and 30 to separate and integrate light by each of the prisms separately. The Wollaston prisms 16a, 16b, and 30 according to the embodiments of the present invention may be birefringence prisms.

An example of installing the Wollaston prisms 16a, 16b, and 30 will be described below in detail.

The objective lens 17 may converge light separated from the Wollaston prism 16a. For example, the objective lens 17 may be a convex lens but is not limited thereto.

Before polarized light arrives at the objective lens 17, a beam splitter 18 may be disposed. The beam splitter 18 may refract light by 90°. In FIG. 3, when the Wollaston prism 16a is disposed close to the objective lens 17, light polarized by the first polarizing plate 15 may be refracted by the beam splitter 18 by a preset angle and may enter the Wollaston prism 16a. Also, the beam splitter 18 transmits light reflected by the eyeball 1 and integrated passing through the Wollaston prism 16a. The light processing means 20 includes a wavefront sensor 22 and a light compensation mirror 21.

The wavefront sensor 22 is configured to sense an astigmatism aberration of light reflected by the eyeball 1. Also, the wavefront sensor 22 reads a wavefront distorted by the astigmatism aberration.

The light compensation mirror 21 compensates light for the astigmatism aberration sensed by the wavefront sensor 22. The light compensation mirror 21 may be an adaptive mirror. A second polarizing plate may be disposed close to a light compensation mirror. In FIG. 3, an example in which light passing through the Wollaston prism 16a and the beam splitter 18 is detected by the second polarizing plate 40 and the light detected by the second polarizing plate 40 is provided to the light compensation mirror 21.

The light processing means 20 overcomes an optical astigmatism aberration which occurs when light passes through the crystalline lens 3 and the vitreous body 5 of the eyeball 1 and is reflected by the retina 1a and provides a wide field of view. The light processing means 20 may be an adaptive optics (AO) technology. The AO technology is generally utilized for imaging of celestial bodies and life.

The light compensated by the light processing means 20 may enter a charge-coupled device (CCD) 9. The CCD 9 is configured to detect light.

The Wollaston prism 16a may be formed as one and may be disposed close to the objective lens 17. When the Wollaston prism 16a is formed as one, as described above, the Wollaston prism 16a may be disposed between the first polarizing plate 15 and the objective lens 17. Referring to FIG. 3, an example is illustrated, in which the Wollaston prism 16a is disposed close to the objective lens 17. Due to this, light emitted by the light source 14 passes through the first polarizing plate 15 and is changed in path by a preset angle by the beam splitter 18 and then passes through the Wollaston prism 16a and the objective lens 17 to be emitted toward the eyeball 1.

When the Wollaston prism 16a is formed as one, polarized light passing through the first polarizing plate 15 is separated by the Wollaston prism 16a. The separated light passes through the objective lens 17 to arrive at the eyeball 1, passes through the crystalline lens 3 and the vitreous body 5, and is reflected by the retina 1a. The reflected light passes through the Wollaston prism 16a and is again integrated as one.

When the Wollaston prism 16a is formed as one, the first light and the second light which have been divided by the Wollaston prism 16a are reflected by the eyeball 1 and return. The first light and the second light meet each other at the Wollaston prism 16a, with offset differences perpendicular to the propagating paths. Here, an optical distance difference generated by a step and a density difference between the first light and the second light on their paths forms phase shift, and interference occurs when the first light and the second light pass through the Wollaston prism 16a. A wavefront 4 reflected by the retina 1a configured as described above and wavefronts 2 which occur at the crystalline lens 3 and the vitreous body 5 are sensed by the wavefront sensor 22, and signals are compensated through the light compensation mirror 21. The beam splitter 18 may be disposed between the wavefront sensor 22 and the light compensation mirror 21 and may transmit a part of the light which passes and may reflect another part of the light between the wavefront sensor 22 and the light compensation mirror 21.

When the Wollaston prism 16a is formed as one, the second polarizing plate 40 may be disposed between the Wollaston prism 16a and the light compensation mirror 21 to allow light reflected by the retina 1a to pass through the second polarizing plate 40 and then arrive at the light compensation mirror 21. The second polarizing plate 40 may be used to check degree of polarization of the light and a direction of polarized plane. The second polarizing plate 40 may be disposed to allow polarized angle with the first polarizing plate 15 to be 90 degrees. This is to minimize a light-leakage phenomenon. Thereby, only signals causing interference through a Wollaston prism may enter the CCD. Also, the second polarizing plate 40 absorbs light oscillating in a particular direction and transmits only a polarized component to the light compensation mirror 21.

Hereinafter, another example of the retinal disease detection apparatus 200 according to the embodiment of the present invention will be described. A part of the descriptions of FIGS. 1 and 3 different from one embodiment described above will be mainly described, and an undescribed part is to be substituted by the above description.

In the embodiment of FIGS. 2 and 4, the light imaging means 10 does not include the second polarizing plate 40, and the second polarizing plate 40 is disposed close to a second Wollaston prism 30.

As described above, according to another example of the cell-level retinal disease detection apparatus 200 according the embodiment of the present invention, the Wollaston prism 16b of a light imaging means 10b may be disposed close to the first polarizing plate 15. Here, the Wollaston prism 16b may be referred to as a first Wollaston prism 16b and will be described with being differentiated from the second Wollaston prism 30 which is a separate Wollaston prism. The first Wollaston prism 16b is disposed close to the first polarizing plate 15 and separates light polarized passing through the first polarizing plate 15 into first light and second light of two paths. The first light and the second light which are separated pass through the objective lens 17, pass through the crystalline lens 3 and the vitreous body 5 at the eyeball 1, and are reflected by the retina 1a. Astigmatism aberrations of the first light and the second light reflected by the retina 1a are sensed by the wavefront sensor 22 and compensated by the light compensation mirror 21.

The second Wollaston prism 30 integrates light compensated by the light processing means 20. The second Wollaston prism 30 is a Wollaston prism formed separately from the first Wollaston prism 16b of the light imaging means 10b. The first light and the second light are compensated by the light compensation mirror 21, and the compensated first and second lights are integrated into one light by the second Wollaston prism 30.

Accordingly, since the light compensation mirror 21 compensates the wavefront 4 reflected by the retina 1a and the wavefront 2 generated by the crystalline lens 3 and the vitreous body 5 before being combined with each other, the wavefront 4 and the wavefront 2 are sensed by the wavefront sensor 22 without a mutual interference effect, thereby reducing an error during compensation by the light compensation mirror 21.

When the cell-level retinal disease detection apparatus 200 includes the first and second Wollaston prisms 16b and 30, unlike the above described embodiment, the second polarizing plate 40 may be disposed close to the second Wollaston prism 30 to detect light passing through the second Wollaston prism 30.

The second polarizing plate 40 may detect light passing through the second Wollaston prism 30 for checking a degree of polarization and a direction of a polarizing plane and may absorb light oscillating in a particular direction to transmit a polarized component.

The cell-level retinal disease detection apparatuses 100 and 200 described above are not limited to the configurations and methods according to the embodiments described above, and all or a part of the embodiments may be selectively combined and configured to have various modifications.

According to the embodiments of the present invention, when a narrow observation view is provided due to an obvious difference between a precise focus and unclear focus caused by a curvature of a retina, it is possible to improve quality of an image by compensating for astigmatism aberrations which occur at a cornea and a crystalline lens when being applied an actual eyeball model.

Also, since an astigmatism difference is sensed by a wavefront sensor and compensated by a light compensation mirror, a wide observation view and high resolution may be provided.

It is obvious to one of ordinary skill in the art that the present invention may be embodied as other particular forms without departing from the concept and essential features of the present invention. Accordingly, the above detailed description should be understood not to be limiting but considered only to be exemplary. The scope of the present invention should be determined by reasonably analyzing the following claims, and all modifications within an equivalent range of the present invention are included in the scope of the present invention.

What is claimed is:

1. A cell-level retinal disease detection apparatus comprising:
 a light imaging part configured to emit light toward an eyeball; and
 a light processing part configured to receive light reflected by the eyeball and to process and compensate light for an astigmatism aberration thereof which occurs at the eyeball,
 wherein the light processing part comprises:
 a wavefront sensor configured to sense the astigmatism aberration of the reflected light which occurs due to the eyeball; and
 a light compensation mirror configured to compensate the light based on the sensed astigmatism aberration and to compensate for a difference in the astigmatism aberration to detect a disease of a retina of the eyeball,
 wherein the light imaging part comprises:
 a first polarizing plate configured to polarize light emitted from a light source in one direction;
 a first Wollaston prism disposed close to the first polarizing plate and configured to separate the polarized light;
 a second Wollaston prism disposed close to the light processing part and configured to obtain interference of a light signal by transmitting light compensated by the light processing part; and
 an objective lens configured to transmit and to converge the light separated by the Wollaston prism.

2. The apparatus of claim 1, wherein the Wollaston prism is disposed close to the objective lens, and the light polarized by the first polarizing plate is refracted by a predetermined angle by a beam splitter and enters the Wollaston prism.

3. The apparatus of claim 2, wherein the light reflected by the eyeball is detected by a second polarizing plate after passing through the Wollaston prism, and the detected light enters the light processing part.

4. The apparatus of claim 1, wherein a second polarizing plate is disposed close to the second Wollaston prism, and
 wherein the second polarizing plate detects light passing through the separate second Wollaston prism.

5. The apparatus of claim 1, wherein at least a part of the light compensated by the light compensation mirror is refracted by a predetermined angle by a beam splitter.

* * * * *